(12) United States Patent
Lazar

(10) Patent No.: US 10,107,881 B2
(45) Date of Patent: Oct. 23, 2018

(54) THERMOSTABILIZATION OF ANTENNA ARRAY FOR MAGNETIC RESONANCE TOMOGRAPHY

(71) Applicant: Razvan Lazar, Erlangen (DE)

(72) Inventor: Razvan Lazar, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 989 days.

(21) Appl. No.: 14/456,422

(22) Filed: Aug. 11, 2014

(65) Prior Publication Data

US 2015/0042339 A1    Feb. 12, 2015

(30) Foreign Application Priority Data

Aug. 12, 2013  (DE) .................... 10 2013 215 918

(51) Int. Cl.
    *G01R 33/385*    (2006.01)
    *A61B 5/055*    (2006.01)
    *G01R 33/34*    (2006.01)

(52) U.S. Cl.
    CPC .......... *G01R 33/3856* (2013.01); *A61B 5/055* (2013.01); *G01R 33/3403* (2013.01)

(58) Field of Classification Search
CPC .. G01R 33/3403; G01R 33/3856; A61B 5/055
See application file for complete search history.

(56) References Cited

U.S. PATENT DOCUMENTS

| | | | | |
|---|---|---|---|---|
| 4,660,013 A * | 4/1987 | Laskaris | ................... | H01F 7/20 324/318 |
| 6,100,693 A | 8/2000 | Eberler et al. | | |
| 6,437,570 B2 * | 8/2002 | Marek | ................... | G01R 33/30 324/300 |
| 6,441,617 B2 * | 8/2002 | Marek | ................... | G01R 33/30 324/300 |
| 6,466,019 B2 * | 10/2002 | Marek | ................... | G01R 33/30 324/318 |

(Continued)

FOREIGN PATENT DOCUMENTS

| | | |
|---|---|---|
| DE | 19722387 A1 | 12/1998 |
| JP | 2002345775 A | 12/2002 |
| WO | 2008105477 A1 | 9/2008 |

OTHER PUBLICATIONS

German Office Action for German Application No. 10 2013 215 918.8 dated Jun. 5, 2014, with English Translation.

(Continued)

*Primary Examiner* — Dixomara Vargas
(74) *Attorney, Agent, or Firm* — Lempia Summerfield Katz LLC

(57) ABSTRACT

A device for thermal stabilization of a first electrical characteristic of an antenna array of a magnetic resonance tomograph includes a heat exchanger configured for thermal coupling of a component of the device to a heat source. The device also includes a temperature-dependent second electrical characteristic. In a predefined connection to the antenna array, the temperature-dependent second electrical characteristic is configured to compensate for an effect of a temperature-dependent change on the first electrical characteristic of the antenna array in a predetermined temperature range.

12 Claims, 2 Drawing Sheets

(56) References Cited

U.S. PATENT DOCUMENTS

| | | | | |
|---|---|---|---|---|
| 6,525,537 B2* | 2/2003 | Nerreter | ............. | G01R 33/3856 |
| | | | | 324/318 |
| 7,141,979 B2* | 11/2006 | Marek | .............. | G01R 33/34076 |
| | | | | 324/322 |
| 7,307,421 B2* | 12/2007 | Kurome | ............. | G01R 33/3854 |
| | | | | 324/318 |
| 7,309,987 B2* | 12/2007 | Lukens | ................. | G01R 33/34 |
| | | | | 324/315 |
| 7,403,007 B1* | 7/2008 | Lim | ................ | G01R 33/34015 |
| | | | | 324/307 |
| 7,471,087 B2* | 12/2008 | Fukuda | ............ | G01R 33/34053 |
| | | | | 324/318 |
| 7,609,064 B2* | 10/2009 | Fukuda | .............. | G01R 33/3657 |
| | | | | 324/307 |
| 7,808,242 B2* | 10/2010 | Yamamoto | ....... | G01R 33/34053 |
| | | | | 324/318 |
| 8,305,079 B2* | 11/2012 | Iwasa | ................ | G01R 33/3804 |
| | | | | 324/315 |
| 2010/0103055 A1 | 4/2010 | Waku et al. | | |

OTHER PUBLICATIONS

Chinese Office Action for Chinese Application No. 201410395010. X, dated Feb. 26, 2018, with English Translation.

* cited by examiner

THERMOSTABILIZATION OF ANTENNA ARRAY FOR MAGNETIC RESONANCE TOMOGRAPHY

RELATED APPLICATIONS

This application claims the benefit of German Patent Application No. DE 102013215918.8, filed Aug. 12, 2013. The entire contents of the priority document are hereby incorporated herein by reference.

TECHNICAL FIELD

The present teachings relate generally to devices for thermal stabilization of a first electrical characteristic of an antenna array of a magnetic resonance tomograph. The present teachings further relate to antenna systems and magnetic resonance tomographs including such devices.

BACKGROUND

Magnetic resonance measurements involve observing the interaction of magnetic moments of atomic nuclei (e.g., nuclear spins) with an external magnetic field.

When excited by an external alternating electromagnetic field around the axis of magnetic field orientation, nuclear spins align themselves in the external agnetic field and precess at a Larmor frequency that depends on the value of the magnetic moment of the nucleus and the external magnetic field. The atomic nuclei then generate an electromagnetic alternating field at the Larmor frequency.

The external alternating electromagnetic field used to excite the nuclear spins is projected into a sample or into a patient via one or a plurality of antenna arrays. One antenna array is a body coil that encircles the patient or the sample. However, local coils that are disposed directly on the patient or on the sample may be used. The electromagnetic field generated by the atomic nuclei is likewise received by the antenna arrays. The same antenna array may receive the signal that has been generated. Alternatively, the nuclear spins may be generated with one type of antenna and the electromagnetic alternating field generated by the atomic nuclei may be received using a different type of antenna.

The efficiency of projection and the sensitivity of reception are dependent on a plurality of characteristics of an antenna array (e.g., the electrical characteristics thereof). Characteristics of the antenna array may be the resonant frequency or the impedance. These characteristics of the antenna array are also dependent on the temperature of the antenna array and the components thereof. Thus, the inductance of a coil or the capacitance of a capacitor may be changed as a result of thermal expansion.

In the construction of the antenna arrays, the elements used may have a temperature coefficient that is equal to or close to zero for the mechanical or electrical characteristics.

The consequences of changes are also offset by control mechanisms. For example, lower reception sensitivity and/or transmission efficiency when the resonant frequency has changed may be compensated for by greater transmitting speed or input amplification.

However, the electrical characteristics may not always be kept constant using components having a low temperature coefficient because the characteristics of the antenna array also depend on the environment.

A body coil may be provided on a cylindrical element that is disposed concentrically between the patient or the sample and the gradient coils. The gradient coils do not prevent alternating electromagnetic fields from being beamed down onto the patient. In order to reduce external interactions with the gradient coils (e.g., to prevent irradiation and absorption of high-frequency energy in the gradient coils), a high-frequency shield may be disposed on the inside of a supporting base for the gradient coils. The shield extends between the gradient coils and the body coil. The body coil and the shield interact. For example, facing metal surfaces of the body coil and the shield effect a capacitive coupling. The electromagnetic waves that are transmitted by the antenna array generate eddy currents in the shield. Since the distance between the body coil and the shield changes if the gradient coil, together with the supporting base and the shield located thereon, becomes hotter, the electrical characteristics of the body coil change. The electrical characteristics change even if the body coil were to have a constant temperature or were configured with a temperature coefficient equal to zero.

SUMMARY AND DESCRIPTION

The scope of the present invention is defined solely by the appended claims, and is not affected to any degree by the statements within this summary.

The present embodiments may obviate one or more of the drawbacks or limitations in the related art. For example, in some embodiments, a magnetic resonance tomograph is provided wherein the temperature-related effects on the antenna array are reduced.

A device in accordance with the present teachings configured for the thermal stabilization of a first electrical characteristic of an antenna array of a magnetic resonance tomograph includes a heat exchanger for thermal coupling of a component of the device to a heat source or to the antenna array. All elements that allow heat transfer between the heat source and a component of the device may be used as heat exchangers in accordance with the present teachings. Examples include fasteners, sealing compounds, structural elements that the component is embedded into, and cooling devices pertaining to the heat source (e.g., configured for exchanging heat with the component). The device further includes a temperature-dependent second electrical characteristic that is configured, in a predefined connection to the antenna array, to compensate for an effect of a temperature-dependent change caused by the heat source on the first electrical characteristic of the antenna array in a predefined temperature range. The second electrical characteristic of a circuit that includes a plurality of components may be a temperature-dependent second electrical characteristic in accordance with the present teachings.

In a circuit having a predetermined antenna array, a device in accordance with the present teachings may be in thermal coupling with the antenna array itself or an object that causes a temperature-related change in the first electrical characteristic of the antenna array. A device in accordance with the present teachings may compensate for a change in the first electrical characteristic through a temperature-related change in the second electrical characteristic through connection to the antenna array. The first electrical characteristic of a system that includes the antenna array and a device in accordance with the present teachings remains substantially unchanged in a predefined temperature range. The phrase "substantially unchanged" as used in this context refers to the value of the first electrical characteristic changing only slightly (e.g., by a maximum of 1%, 2%, 5% or 10%). A temperature range in accordance with the present teachings may encompass temperatures between 20° C. and 30° C., 20° C. and 40° C., and 15° C. and 50° C.

An antenna system in accordance with the present teachings has a device in accordance with the present teachings and an antenna array. The device is thermally coupled to the antenna array via the heat exchanger. The device is electrically connected to the antenna array, such that the antenna system has a substantially unchanged first electrical characteristic in the predefined temperature range.

By thermal coupling between the antenna array and the device, the antenna system in accordance with the present teachings may have properties for the first electrical characteristic that are substantially independent of the temperature in a predefined temperature range.

A magnetic resonance tomograph in accordance with the present teachings includes a device, an antenna array, and a heat source. The heat source is in a cause-and-effect relationship with a temperature-dependent change in the first electrical characteristic. The magnetic resonance tomograph includes a first thermal coupling between the device and the heat source via the heat exchanger. The device is electrically connected to the antenna array, such that an effect of the temperature-dependent change on the first electrical characteristic of the antenna array is substantially offset in a predefined temperature range.

If the change in the first electrical characteristic of the antenna array is not directly dependent on the temperature of the antenna array itself, but rather is indirectly caused by temperature-dependent physical effects on the antenna array, the first electrical characteristic of a system that includes the antenna array and the device may be kept unchanged in a predefined temperature range using a magnetic resonance tomograph and device in accordance with the present teachings.

In some embodiments, a device in accordance with the present teachings includes only passive components. As used herein, the phrase "passive components" refers to components that do not require any further power supply or control signals for utilization and that function apart from a signal to be processed. For example, passive components may be resistors, coils, and capacitors.

Since a device in accordance with the present teachings may have only passive components, the device may be inserted into existing systems.

In some embodiments, the first electrical characteristic is a resonant frequency of the antenna array.

In a resonant antenna array, the efficiency of transmission and the sensitivity of reception of an electromagnetic wave are dependent on the resonant frequency of the antenna array being consistent with the frequency of the electromagnetic wave. Since a device in accordance with the present teachings is configured to compensate for a temperature-related change in the resonant frequency of the antenna array in a predefined temperature range, the device may be used to reduce or eliminate this dependency in a predefined connection to the antenna array.

In some embodiments, the first electrical characteristic is an impedance of the antenna array.

The efficiency of transmission and the sensitivity of the reception of an electromagnetic wave substantially depend on the impedance of the antenna array being aligned with the impedance of the power supply. If the two impedances are not consistent, losses occur as a result of the reflection of the electric signals at the point where the antenna array interfaces with the power supply. Since a device in accordance with the present teachings is configured to compensate for a temperature-related change in the impedance of the antenna array in a predefined temperature range, the device may be used to reduce or eliminate this dependency when in a predefined connection to the antenna array.

In some embodiments, the second electrical characteristic is a capacitance of the device.

A variable capacitance may be used to compensate for different first electrical characteristics in the temperature properties of the circuits by having different circuits. For example, capacitances may be achieved in a small spatial area.

In some embodiments, the heat exchanger is a metal contact surface. A metal contact surface may have a good thermal conductivity.

In some embodiments, the heat exchanger is a conduit for a cooling medium. The conduit may be used to provide a thermal coupling with a device in accordance with the present teachings that does not require direct vicinity and that allows electrical isolation from a heat source.

In some embodiments, the heat source is a gradient coil. A thermal coupling with the gradient coil may be used to compensate for changes in the first electrical characteristic of the antenna array that have been caused by thermal effects (e.g., expansion of the gradient coil) even if the antenna array itself does not become hot.

In some embodiments, the magnetic resonance tomograph further includes a coolant circuit to cool the heat source. The heat exchanger is in thermal contact with the coolant circuit. The coolant circuit may be used to provide a thermal coupling of the heat source with a device in accordance with the present teachings that does not require direct vicinity and that allows electrical isolation from the heat source.

In some embodiments, the first thermal coupling has a first time constant for a first heat transfer between the heat source and the device, and the second thermal coupling between the antenna array and the heat source has a second time constant. The first thermal coupling is configured such that the antenna array has a substantially unchanged first electrical characteristic for a predefined operating profile of the magnetic resonance tomograph.

The heat transfer between the heat source and the device, and the change in the first electrical characteristic that is dependent on a temperature change in the heat source, may have different characteristics. Since the time constants are aligned with one another by design features (e.g., length of the thermal conduction pathways, flow speed of the cooling medium, thermal capacities or electrical characteristics of components), compensation for the first electrical characteristic may be achieved even where there is a dynamic temperature progression in an operating profile of the magnetic resonance tomograph.

DETAILED DESCRIPTION

Figure 1:
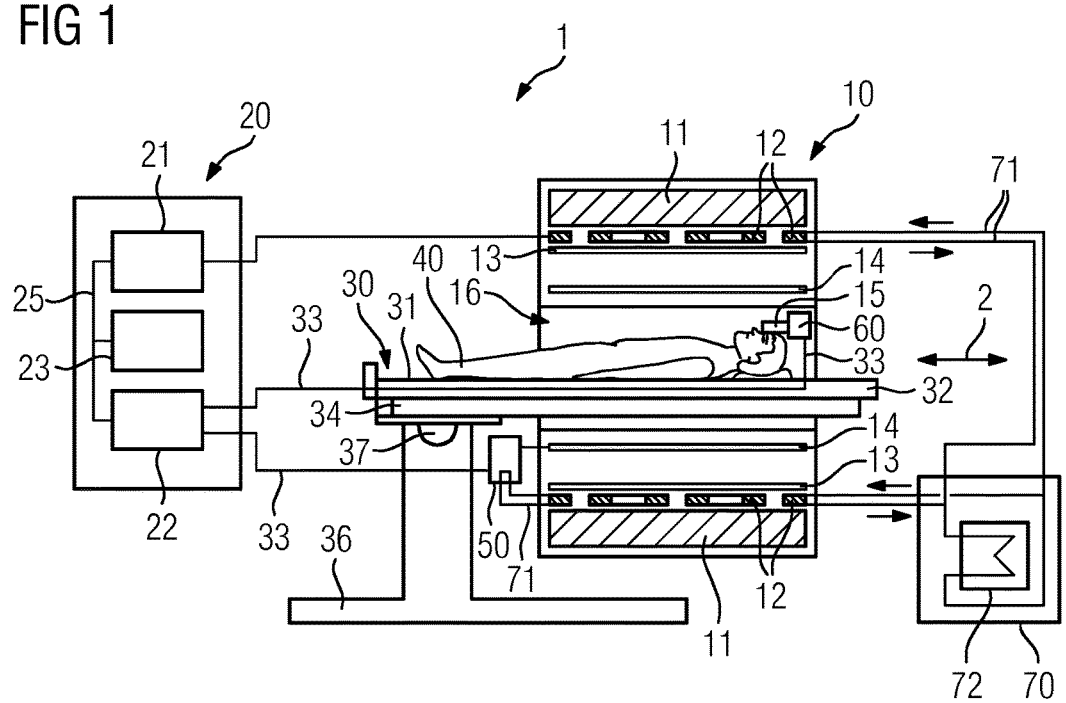
FIG. 1 shows a schematic diagram of an example of a magnetic resonance tomograph 1 in accordance with the present teachings. The exemplary magnetic resonance tomograph 1 includes an example of a device 50 in accordance with the present teachings.

The magnetic resonance tomograph 1 includes a magnet unit 10 with a field magnet 11. The field magnet 11 generates a static magnetic field B0 to direct nuclear spins of samples or of a patient 40 in a sample volume. The sample volume is disposed in a duct 16 that extends in a longitudinal direction 2 through the magnet unit 10. The field magnet 11 may be a superconducting magnet that may provide magnetic fields with a magnetic flow density of up to 3T and, in some machines, even higher. For lower field intensities, permanent magnets or electromagnets with normally conducting coils may be used.

Furthermore, the magnet unit 10 includes gradient coils 12 that are configured to superimpose variable magnetic fields in three spatial directions on the magnetic field B0 in order to spatially differentiate the imaging zones that have been captured in the sample volume. The gradient coils 12 may be coils of normally conducting wires that, in the sample volume, may generate fields that are orthogonal to one another.

On the inside of the gradient coils 12 and disposed towards the sample volume 16, there is a shield 13. The shield 13 has conductivity and substantially prevents propagation of high-frequency electromagnetic waves between the gradient coils 12 and the area located within the shield 13 (e.g., waves that have a frequency range above 1 MHz, as do the waves used in magnetic resonance tomography). The shield 13 is disposed on the gradient coils or on a common supporting base.

The magnet unit 10 also includes a body coil 14 and local coils 15. Both the body coil 14 and the local coils 15 may be referred to as antenna arrays 14, 15 in the description that follows. Both the body coil 14 and the local coils 15 may emit a high-frequency alternating magnetic field into the surrounding area. The body coil 14 is used inter alia as a transmission coil to generate across a large volume a homogeneous electromagnetic excitation field.

The local coils 15 may be arranged as a two-dimensional or three-dimensional matrix and cover parts of the body of the patient 40. The local coils 15 are used inter alia as transmission coils in order to project, in each case, electromagnetic waves into a substantially spatially limited volume of the body. The local coils 15 may, for example, be circular or polygonal coils that partially overlap one another. The fields of adjacent coils may be partially superimposed on one another (e.g., some in the same direction and some in opposite directions), such that adjacent coils substantially do not interact with one another. The overlapping arrangement of the transmission coils 15 may be used to project an alternating electromagnetic field in the entire area to be examined that is covered by the coils.

A magnetic resonance signal that is generated by the electromagnetic field of the body coil 14 or the local coils 15 and the static magnetic field B0 in the patient may either be picked up again by the local coils 15 or by the separate body coil 14. The separate body coil 14 may receive signals from the entire area that is being investigated.

A control unit 20 supplies the magnet unit 10 with the various signals for the gradient coils 12 and the body coil 14 or the local coils 15. The control unit 20 evaluates the signals that have been received.

The control unit 20 includes a gradient driver 21 that is configured to supply the gradient coils 12 via cables with variable currents that are time-coordinated. The control unit is further configured to provide the desired gradient fields in the sample volume.

The control unit 20 includes a transmitting and receiving unit 22 that is configured to generate a high-frequency pulse with a predefined time progression, amplitude, phase, and spectral power distribution for an antenna array 14, 15 in order to generate a magnetic resonance of the nuclear spins in the patient 40, thereby creating pulse outputs in the kilowatt range.

The transmitting and receiving unit 22 is further configured to evaluate (e.g., for amplitude and phase) high-frequency signals that have been received from the body coil 14 or one or a plurality of local coils 15 and supplied via a signal circuit 33 to the transmitting and receiving unit 22. These signals may be high-frequency signals that transmit nuclear spins in the patient 40 in response to excitation by a high-frequency pulse in the magnetic field B0 or in a magnetic field resulting from a superimposition of B0 and gradient fields.

The control unit 20 further includes a control 23 that is configured to carry out the time coordination of the activities of the gradient driver 21 and the transmitting and receiving unit 22 in order to capture images using magnetic resonance tomography. The control 23 is connected to the other gradient driver 21 and the transmitting and receiving unit 22 via a signal bus 25 in a signal exchange. The control 23 is configured to accept and process signals from inside the patient 40 that have been evaluated by the transmitting and receiving unit 22, or to provide the gradient driver 21 and the transmitting and receiving unit 22 with pulse and signal forms and to coordinate the pulse and signal forms with respect to time.

The patient 40 is placed on a patient table 30 as are used in magnetic resonance tomography. The patient table 30 includes a first supporting strut 36 that is arranged beneath a first end 31 of the patient table 30. To maintain the patient table 30 in a horizontal position, the supporting strut 36 may have a foot that extends along the patient table 30. In order to move the patient table 30, the foot may also include a moving element (e.g., rollers). Apart from the supporting strut 36 at the first end 31, there are no structural components between the floor and the patient table. As a result, the patient table may be slid up as far as the first end 31 into the duct 16 in the field magnet 11. FIG. 1 shows linear rail systems 34 that moveably connect the supporting strut 36 to the patient table 30, such that the patient table 30 may move in a longitudinal direction 2. The linear rail system includes a drive 37 whereby the patient table 30 may be moved in a longitudinal direction 2. The operation is controlled either by an operator or by the control 23. As a result, areas of the patient's body that cover a greater expanse than the sample volume may be investigated in the duct 16.

The magnet unit 10 includes a cooling system 70 that supplies a cooling medium via cooling medium lines 71 to the gradient coils for cooling and then returns the cooling medium via the cooling lines 71 to the cooling system 70. The cooling medium releases heat energy to the cooling system 70 via a heat exchanger 72.

FIG. 1 shows an exemplary first device 50 and an exemplary second device 60 in accordance with the present teachings. The first device 50 and the second device 60 may be used for the thermal stabilization of a first electrical characteristic of an antenna array 14, 15. The first device 50 and the second device 60 shown in FIG. 1 are two exemplary devices that may be connected to a magnetic resonance tomograph 1 in two ways. However, other kinds of connections may be used. For example, the simultaneous representation of the first device 50 and the second device 60 is only one example of a connection.

The device 50 is connected via the signal circuit 33 to the transmitting and receiving unit 22 and to the cooling system 70 via cooling medium conduits 71. The device 50 is arranged in the cooling medium conduit such that the cooling medium heated by the gradient coil 12 flows through the device 50 and has a temperature that indicates a measurement of the temperature of the gradient coil 12 and the shield 13. In some embodiments, the temperature of the cooling medium is equal to the temperature of the gradient coils 12. In other embodiments, a temperature difference in the cooling medium in the device 50 is proportional to a temperature difference between the gradient coil 12 and the ambient temperature. Other correlations may also be used.

Figure 2:
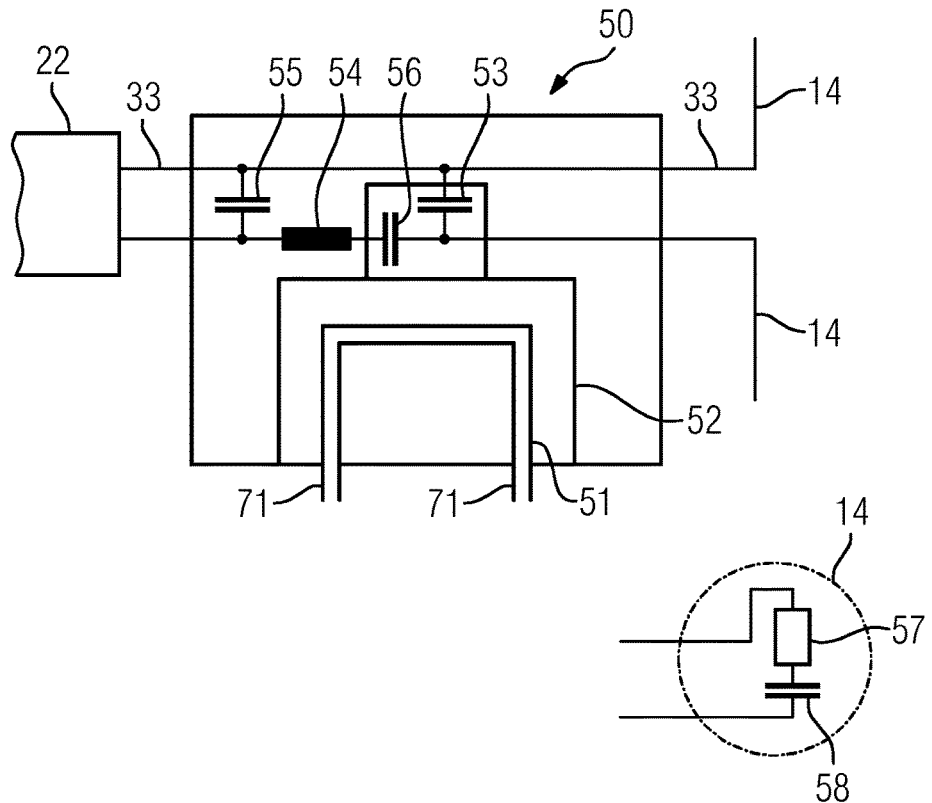
FIG. 2 shows a schematic diagram of an example of a device in accordance with the present teachings.

Further details of the device 50 are depicted in FIG. 2.

Figure 3:
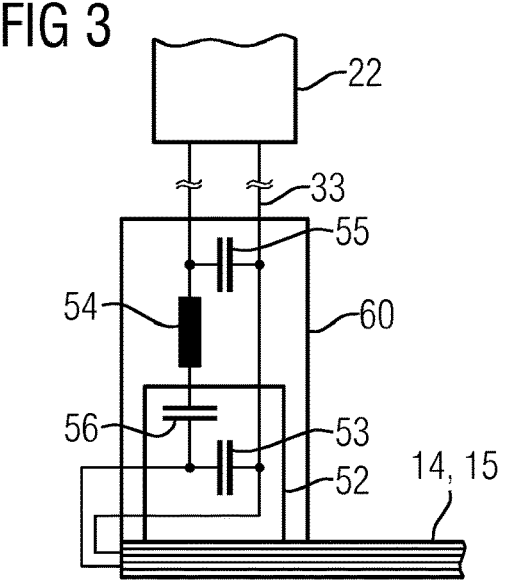
FIG. 3 shows a schematic diagram of an example of an antenna system in accordance with the present teachings.

As shown in FIG. 3, the device 60 is in direct thermal contact with a local coil 15. The device 60 is connected to the signal circuit 33, such that an outgoing or incoming signal from or to the local coil 15 passes through the device 60.

The device 60 may be arranged in direct thermal contact with the body coil 15 and inserted into the signal circuit 33 between the transmitting and receiving unit 22 and the body coil 14.

A plurality of local coils 15 may be used in a magnetic resonance tomograph in accordance with the present teachings. Each individual coil may be provided with a device 60.

In some embodiments, separate devices (e.g., first device 50 and second device 60) may be provided in each case for transmitting and receiving signals. Transmission may occur using the body coil 14, and reception may occur using local coils 15 or vice versa. The first device 50 and the second device 60 may be assigned in each case to the antenna arrays 14, 15.

FIG. 2 shows a schematic diagram of an embodiment of a device 50 in accordance with the present teachings.

The device 50 includes a conduit 51 in a heat exchanger 52. Cooling medium conduits 71 of a cooling system 70 are connectable to the heat exchanger 52. The cooling medium may circulate through the conduit 51. The heat exchanger 52 for thermal coupling may acquire the temperature of the cooling medium.

The device 50 further includes a first capacitor 53 and a third capacitor 56 that are in thermal contact with the heat exchanger 52 and that acquire the temperature of the heat exchanger 52. As a second electrical characteristic, the first capacitor 53 and the third capacitor 56 have a capacity that is dependent on the temperature. Together with the second capacitor 55 and the coil 54, the capacitors 53, 55, 56 form an adaptor box that adapts the impedance of the body coil 14 in the signal circuit 33 to the transmitting and receiving unit 22. The dotted circuit in FIG. 2 shows an equivalent circuit diagram for the body coil 14 with an antenna impedance 56 in series with an antenna capacitor 57.

Through appropriate selection of the temperature coefficient of the first capacitor 53 and the third capacitor 56, compensation for the change in the first electrical characteristic of the body coil 14 caused, for example, by an expansion of the shield 13 may be achieved.

In some embodiments, the body coil 14 includes an antenna impedance 57 of 60 Ohms and an antenna capacity 58 of 20 pF. The power cable has an impedance of 50 Ohms. The first capacitor 53 is configured with a capacity of 10 pF, the second capacitor 55 has a capacity of 26.6 pF, the third capacitor 56 has a capacity of 10 pF, and the coil 54 has an inductance of 265 nH. The coil 54 and the second capacitor 55 have a temperature gradient that is substantially equal to zero and/or the coil 54 and the second capacitor 55 are maintained at a constant temperature by, for example, being thermally isolated from the heat exchanger 52.

In an exemplary magnetic resonance tomograph 1, the gradient coils 12 heat up by 30 degrees centigrade when the gradient coils 12 are in operation. As a result, the temperature of the shield rises by 25 degrees centigrade. The body coil 14 itself heats up by 20 degrees centigrade. The resonant frequency of the body coil drops by 250 kHz. The drop corresponds to an increase in the antenna capacity 58 in the equivalent circuit diagram for the body coil 14 from 20 pF to 20.1 pF.

To compensate for the change, the capacity of the first capacitor 53 rises as a result of being heated up to 10.18 pF, and the capacity of the third capacitor 56 drops to 9.97 pF. If the temperature of the cooling water is equal to the temperature of the capacitors 53, 56, there is a positive temperature coefficient for the first capacitor 53 of $6 *10^{-4}$ l/K, and a temperature coefficient for the third capacitor 56 of $-1*10^{-4}$ l/K.

The capacitors are made, for example, using dielectrics with a low dielectricity constant (e.g., LDC capacitors). For example, special steatites or earthing elements containing rutile ($TiO_2$) are used. The dielectrics of this type are used in the manufacture of temperature-coefficient capacitors. By using additives, the negative temperature coefficient of $TiO_2$ of $-800*10\text{-}6/K$ may be moved up to zero and even into the positive range. With different additives, a further move into the negative range is achieved. In this way, materials with a temperature coefficient of $+100$, $\pm 0$, $-33$, $-75$, $-150$, $-470$ and $-1500*10\text{-}6/K$ are obtained. These materials are known, respectively, as P100, NP0, N33, N075, N150, N470, and N 1500.

Higher positive temperature coefficients may be achieved, for example, by using the dielectric barium titanate $BaTiO_3$ as a base material. Barium titanate has a relative dielectricity constant (DC) of several thousand at a temperature of about 120° C. Above and below this temperature point (e.g., the "Curie point"), the DC drops with a value of 1500 being produced at a temperature of 20° C.

FIG. 3 shows a further embodiment of a device 60 in accordance with the present teachings. The embodiment shown in FIG. 3 differs from the embodiment shown in FIG. 2 in that the heat exchanger does not include a cooling medium conduit. Instead, heat exchange occurs through direct contact. In FIG. 3, elements identical to those shown in FIG. 2 are denoted by the same reference signs.

In FIG. 3, the heat exchanger 52 is in direct contact with the coil. The coil may be a body coil 14 or a local coil 15. The heat exchanger 52 may be disposed directly on the gradient coils 12.

The contact surface for the coil 14, 15 may be a flat surface that is made of metal and abuts onto a corresponding surface of the coil 14, 15. Other complementary surfaces on the coil and the heat exchanger configured to come into full surface contact with each other may be used instead of a flat surface. In some embodiments, the heat exchanger 52 may include a bolt that is screwed into a corresponding thread on the coil.

In some embodiments, the heat exchanger 52 may be formed by a component of the coil 14, 15 or gradient coil 12 or of the shield 13 thereof. The capacitor or capacitors 53, 56 may be embedded, for example, in an epoxide resin that forms the structure of the gradient coil 12 or the coils 14, 15.

Because the coil 54 and the second capacitor 55 are in the direct vicinity of the heat source, the coil 54 and the second capacitor 55 may not be prevented from heating up even with thermal insulation. In the embodiment shown in FIG. 3, the elements 54, 55 may have a temperature coefficient that is substantially zero. The elements 54, 55 interacting in the circuitry provided may compensate reciprocally for the thermal changes in their electrical values.

In some embodiments, a device in accordance with the present teachings may be configured as a component of the coils 14, 15. For example, the device may be completely embedded in a casting resin that forms a coil body of the body coil 14 or of the local coil 15.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A device for thermal stabilization of a resonant frequency or an impedance of an antenna array of a magnetic resonance tomograph, the device comprising:
   a heat exchanger configured for thermal coupling of a component of the device to a heat source or to the antenna array; and
   a temperature-dependent capacitance;
   wherein the device is connected to the antenna array; and
   wherein the device is configured to compensate for an effect of a temperature-dependent change on the resonant frequency or the impedance of the antenna array in a predefined temperature range, the temperature-dependent change caused by the heat source.

2. The device of claim 1, wherein the device comprises only passive components.

3. The device of claim 2, wherein the heat exchanger comprises a metallic contact surface.

4. The device of claim 2, wherein the heat exchanger comprises a metallic contact surface.

5. The device of claim 2, wherein the heat exchanger comprises a metallic contact surface.

6. The device of claim 1, wherein the heat exchanger comprises a metallic contact surface.

7. The device of claim 1, wherein the heat exchanger comprises a conduit for a cooling fluid.

8. An antenna system comprising:
   a device for thermal stabilization of a resonant frequency or an impedance of an antenna array of a magnetic resonance tomograph; and
   an antenna array;
   wherein the device comprises:
      a heat exchanger configured for thermal coupling of a component of the device to a heat source or to the antenna array; and
      a temperature-dependent capacitance;
   wherein the device is connected to the antenna array; and
   wherein the device is configured to compensate for an effect of a temperature-dependent change on the resonant frequency or the impedance of the antenna array in a predefined temperature range, the temperature-dependent change caused by the heat source;
   wherein the device is thermally coupled via the heat exchanger to the antenna array; and
   wherein the device is electrically connected to the antenna array, such that an effect of the temperature-dependent change in the resonant frequency or the impedance of the antenna array is substantially offset in the predefined temperature range.

9. A magnetic resonance tomograph, comprising:
   a device for thermal stabilization of a resonant frequency or an impedance of an antenna array of a magnetic resonance tomograph, the device comprising:
      a heat exchanger configured for thermal coupling of a component of the device to a heat source or to the antenna array; and
      a temperature-dependent capacitance;
      wherein the device is connected to the antenna array; and
      wherein the device is configured to compensate for an effect of a temperature-dependent change on the resonant frequency or the impedance of the antenna array in a predefined temperature range, the temperature-dependent change caused by the heat source;
   an antenna array;
   a heat source; and
   a first thermal coupling between the device and the heat source via the heat exchanger;
   wherein the heat source is in a cause-and-effect relationship with the temperature-dependent change in the resonant frequency or the impedance; and
   wherein the device is electrically connected to the antenna array, such that the effect of the temperature-dependent change in the resonant frequency or the impedance of the antenna array is substantially offset in the predefined temperature range.

10. The magnetic resonance tomograph of claim 9, wherein the heat source comprises a gradient coil.

11. The magnetic resonance tomograph of claim 10, further comprising:
   a coolant circuit configured to cool the heat source;
   wherein the heat exchanger is in thermal contact with the coolant circuit.

12. The magnetic resonance tomograph of claim 9, wherein the first thermal coupling comprises a first time constant for a first heat transfer between the heat source and the device; wherein a second thermal coupling between the antenna array and the heat source comprises a second time constant; and wherein the first thermal coupling is configured such that the resonant frequency or the impedance of the antenna array is substantially unchanged for a predefined operating profile of the magnetic resonance tomograph.

* * * * *